US009084638B2

(12) United States Patent
Linares

(10) Patent No.: US 9,084,638 B2
(45) Date of Patent: Jul. 21, 2015

(54) IMPLANT FOR PROVIDING INTER-VERTEBRAL SUPPORT AND FOR RELIEVING PINCHING OF THE SPINAL NERVES

(71) Applicant: Linares Medical Devices, LLC, Auburn Hills, MI (US)

(72) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 114 days.

(21) Appl. No.: 13/891,001

(22) Filed: May 9, 2013

(65) Prior Publication Data

US 2013/0253583 A1   Sep. 26, 2013

Related U.S. Application Data

(63) Continuation-in-part of application No. 12/614,472, filed on Nov. 9, 2009, now abandoned.

(60) Provisional application No. 61/112,959, filed on Nov. 10, 2008.

(51) Int. Cl.
*A61B 17/70* (2006.01)
*A61F 2/44* (2006.01)
(Continued)

(52) U.S. Cl.
CPC ............. *A61B 17/7064* (2013.01); *A61B 17/70* (2013.01); *A61F 2/4405* (2013.01); *A61B 17/562* (2013.01); *A61F 2002/30016* (2013.01); *A61F 2002/3093* (2013.01); *A61F 2002/30448* (2013.01); *A61F 2002/30563* (2013.01); *A61F 2002/30607* (2013.01); *A61F 2002/30616* (2013.01); *A61F 2002/30841* (2013.01); *A61F 2002/30904* (2013.01); *A61F 2250/0019* (2013.01)

(58) Field of Classification Search
CPC .. A61B 17/7064; A61B 17/70; A61B 17/562; A61F 2/4405; A61F 2002/30016; A61F 2002/30563; A61F 2002/30616; A61F 2002/30904; A61F 2002/3093; A61F 2250/0019; A61F 2002/30448; A61F 2002/30607; A61F 2002/30841
USPC .................. 606/74, 246, 247, 279, 280, 281; 623/17.11–17.16
See application file for complete search history.

(56) References Cited

U.S. PATENT DOCUMENTS

| 4,554,914 A | 11/1985 | Kapp et al. |
| 4,697,582 A | 10/1987 | William |
| 5,084,048 A | 1/1992 | Jacob et al. |

(Continued)

*Primary Examiner* — Pedro Philogene
(74) *Attorney, Agent, or Firm* — Douglas J. McEvoy

(57) ABSTRACT

An implant for assisting in providing a correct separation distance between overlapping superior and inferior articular processes, such as associated with succeeding lumbar vertebrae (L1-L5). The implant teaches a pocket defining body having an open rim profile of variable wall thickness, the implants being employed individually or in paired fashion between each laterally spaced pair of overlapping facet contact locations established between inwardly facing superior articular process facets associated with a first (lower) vertebra and opposing outwardly facing inferior articular process facets associated with a second (upper succeeding) vertebra. Use of the implant assists in providing correct lateral spacing between the superior and inferior processes, reducing or preventing pinching of the laterally extending nerve branches of the spinal nerve column.

5 Claims, 9 Drawing Sheets

(51) Int. Cl.
   *A61B 17/56*    (2006.01)
   *A61F 2/30*    (2006.01)

(56) References Cited

U.S. PATENT DOCUMENTS

| | | | |
|---|---|---|---|
| 5,540,690 A | 7/1996 | Miller et al. | |
| 5,645,599 A | 7/1997 | Samani | |
| RE36,758 E * | 6/2000 | Fitz | 623/17.11 |
| 6,132,431 A | 10/2000 | Nilsson et al. | |
| 7,510,567 B2 | 3/2009 | Zucherman et al. | |
| 7,537,611 B2 * | 5/2009 | Lee | 623/17.11 |
| 7,585,316 B2 | 9/2009 | Trieu | |
| 7,588,592 B2 | 9/2009 | Winslow et al. | |
| 7,608,106 B2 | 10/2009 | Reiley | |
| 7,618,453 B2 | 11/2009 | Goble et al. | |
| 7,621,955 B2 | 11/2009 | Goble et al. | |
| 7,651,515 B2 | 1/2010 | Mack et al. | |
| 7,658,753 B2 | 2/2010 | Carl et al. | |
| 8,105,357 B2 * | 1/2012 | Bruneau et al. | 606/248 |
| 8,246,684 B2 * | 8/2012 | Lee | 623/17.15 |
| 2005/0019093 A1 | 1/2005 | Knight | |
| 2006/0149228 A1 | 7/2006 | Schlapfer et al. | |
| 2006/0229607 A1 | 10/2006 | Brumfield | |
| 2006/0293751 A1 | 12/2006 | Lotz et al. | |
| 2007/0093814 A1 | 4/2007 | Callahan et al. | |
| 2007/0093815 A1 | 4/2007 | Callahan et al. | |
| 2007/0112428 A1 | 5/2007 | Lancial | |
| 2007/0161990 A1 | 7/2007 | Hillyard et al. | |
| 2007/0270827 A1 | 11/2007 | Lim et al. | |
| 2008/0177308 A1 | 7/2008 | McLeer | |
| 2009/0326592 A1 | 12/2009 | Butler et al. | |

\* cited by examiner

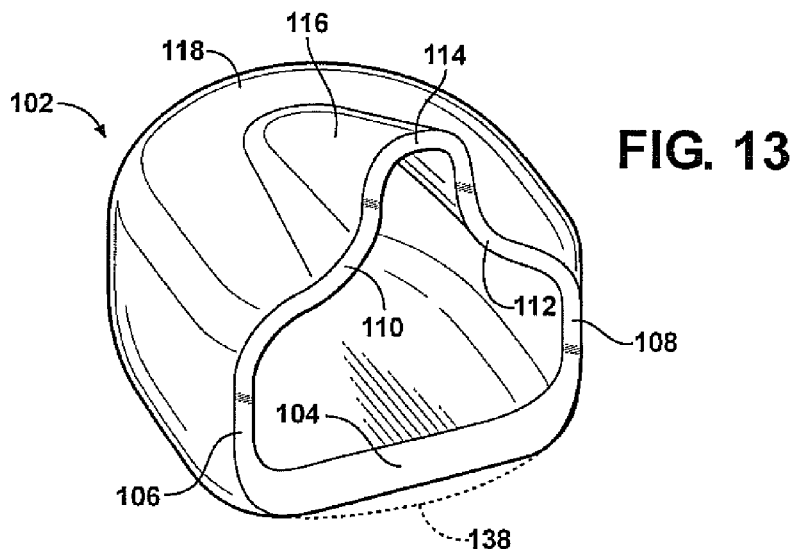
FIG. 13
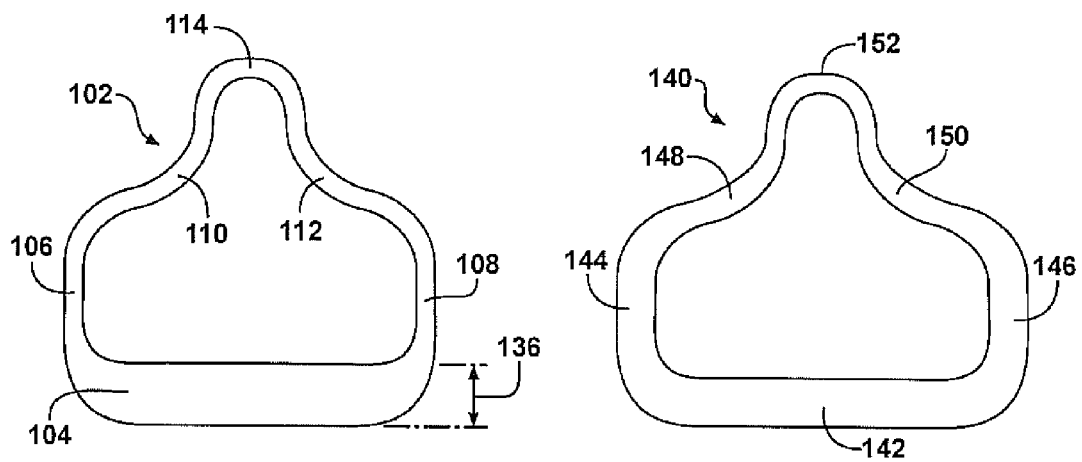
FIG. 14
FIG. 15
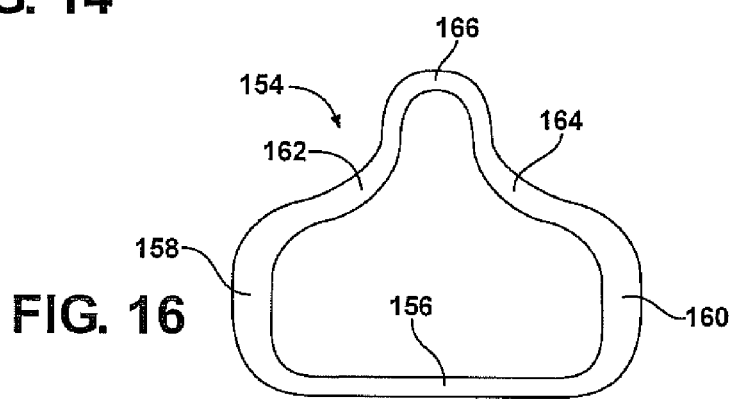
FIG. 16

IMPLANT FOR PROVIDING INTER-VERTEBRAL SUPPORT AND FOR RELIEVING PINCHING OF THE SPINAL NERVES

CROSS-REFERENCE TO RELATED APPLICATIONS

This application is a Continuation-in-part of application Ser. No. 12/614,472 filed on Nov. 9, 2009. Application Ser. No. 12/614,472 claims the benefit of U.S. Provisional Application 61/112,959 filed on Nov. 10, 2008, the contents of which are incorporated herein in their entirety.

FIELD OF THE INVENTION

The present invention discloses an implant for assisting in providing a correct separation distance between overlapping superior and inferior articular processes, such as associated with succeeding lumbar vertebrae (L1-L5). More specifically, the present invention teaches a pocket defining insert having a variable wall thickness and which are employed individually or in paired fashion between each laterally spaced pair of overlapping facet contact locations established between inwardly facing superior articular process facets associated with a first (lower) vertebra and opposing outwardly facing inferior articular process facets associated with a second (upper succeeding) vertebra. Use of the pocket inserts assists in providing correct lateral spacing between the opposing facet surfaces associated with the superior and inferior articular processes, this assisting in reducing or preventing pinching of the laterally extending nerve branches of the spinal nerve column.

DESCRIPTION OF THE BACKGROUND ART

The prior art is documented with examples of spinal support plates and the like. In a most common example, a titanium plate is utilized and which his attached, such as by bone screws, to succeeding vertebral locations in order to fuse, or immobilize, a given area of the spine. Shortcomings associated with the installation of such fixed plates include both the pain and discomfort of implantation, along with the subsequent loss of flexibility.

A further problem associated with a lateral misalignment condition existing between the vertebrae is pinching of the lateral nerve branches of the spinal column. This problem is particularly severe in respects to the seating arrangement established between the (inwardly facing) superior articular process facets and above-succeeding and overlapping (outwardly facing) inferior articular process facets of the inter-lumbar vertebrae (L1-L5).

Among the prior art is U.S. Pat. No. 5,571,191, to Fitz, which teaches an artificial facet joint incorporating both of a conical or pyramidal shaped superior component which is fastened to and over a distal tip of an inferior articular process. A corresponding inferior component further mounts over the superior articular process and exhibits a configured low-friction surface for abutting the superior component.

SUMMARY OF THE INVENTION

The present invention discloses an implant for assisting in providing a correct separation distance between overlapping superior and inferior articular processes, such as associated with succeeding lumbar vertebrae (L1-L5). The implant teaches a three dimensional shaped body, such as constructed of a flexible plastic of other suitable material, and exhibiting an annular open rim profile defining a pocket defining shape having a variable wall thickness.

The body includes an arcuate and three dimensional shaped body exhibiting a plurality of rounded edges and which are configured in one embodiment to exhibit an open rim edge establishing an extending interior and such that each body can mount over a tips of an associated inferior articular processes. In this fashion, the implant bodies can be employed individually or in paired fashion between each laterally spaced pair of overlapping facet contact locations established between inwardly facing superior articular process facets associated with a first (lower) vertebra and opposing outwardly facing inferior articular process facets associated with a second (upper succeeding) vertebra. Use of the pocket implant assists in providing correct lateral spacing between the opposing facet surfaces associated with the superior and inferior articular processes, this assisting in reducing or preventing pinching of the laterally extending nerve branches of the spinal nerve column.

BRIEF DESCRIPTION OF THE DRAWINGS

Reference will be made to the attached drawings, when read in combination with the following detailed description, wherein like reference numerals refer to like parts throughout the several views, and in which:

FIG. 13 is a perspective view of a selected pocket shaped implant exhibiting an open rim profile and peak edge configuration for facilitating mounting over an extending tip of the inferior process;

FIG. 14 is an end view illustration of the pocket implant of FIG. 13;

FIG. 15 is an end view illustration a variation of implant exhibiting a different edge extending profile and associated wall thickness, such as for accommodating a different spatial relationship established between articulating superior/inferior processes; and FIG. 16 is a further end view variation of a pocket implant similar to those depicted in FIGS. 14-15 and illustrating different wall thicknesses.

DETAILED DESCRIPTION OF THE PREFERRED EMBODIMENTS

Referring now to the several illustrations, the present invention discloses a stabilizing brace for securing any number of thoracic vertebrae. As will be described throughout the succeeding embodiments, the brace is intended to provide any desired range of flexibility in application (as well as establishing substantial stationary immobilizing effect on the vertebrae in which it is installed).

As will be further described, the brace can be provided individually or in a paired fashion and in order to prevent a given range of undesirable inter-movement of misaligned vertebrae, such movement being beyond a lesser range which may be desired and such as which may result in great pain in instances where impacting of the spinal nerve (not shown) and associated branches is involved, this without the necessity of permanently and fixedly fusing the vertebrae in place. As will be described in reference FIGS. 8 and 9, additional features such as inter-vertebral supporting inserts can be incorporated in combination with the stabilizing brace and which provide additional biasing support at such at the interface between opposing superior and inferior articular processes associated with succeeding vertebrae at the regions in which they normally contact each other.

Figure 7:
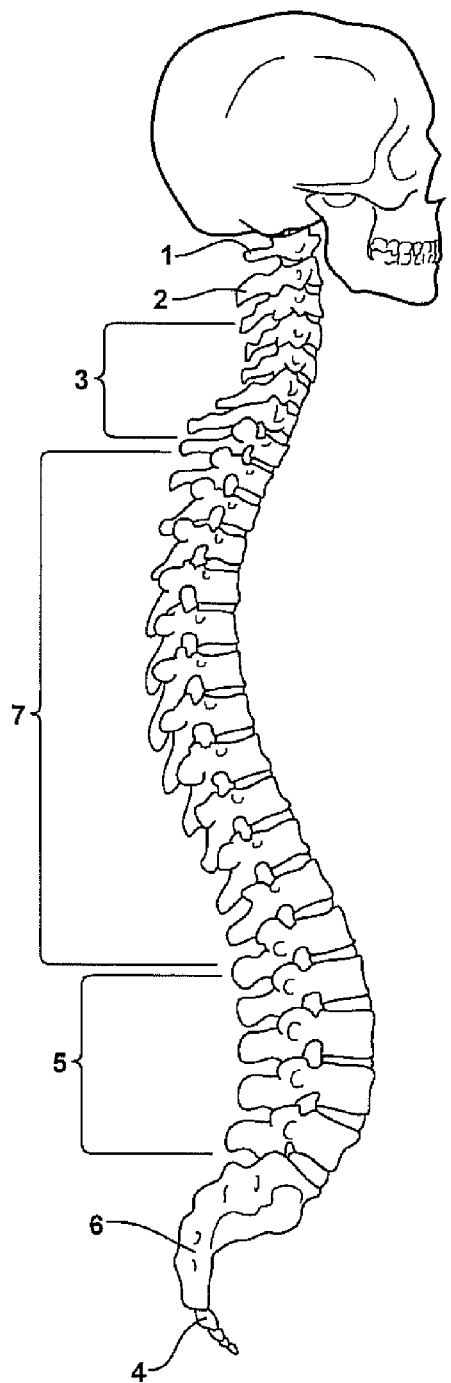
FIG. 7 is a side plan illustration of the known prior art and referencing the positioning of the twelve thoracic vertebrae, collectively vertebral range 7, in relation to the various upper curve cervical vertebrae 1, 2, 3 and the lower positioned lumbar vertebrae 5, sacrum 6 and coccygeal vertebrae 4.

Referring first to FIG. 7, a side plan illustration is shown of the known prior art and referencing the positioning of the twelve thoracic vertebrae, collectively vertebral range 7, in relation to the various upper curve cervical vertebrae 1, 2, 3 and the lower positioned lumbar vertebrae 5, sacrum 6 and coccygeal vertebrae 4. The twelve thoracic vertebrae compose the middle segment of the vertebral column, between the cervical vertebrae and the lumbar vertebra.

The thoracic vertebrae are intermediate in size between those of the cervical and lumbar regions, with increasing size proceeding down the spine, the upper vertebrae being much smaller than those in the lower part of the region. As further shown in the prior art illustration of FIG. 7A, selected thoracic vertebrae is further distinguished by the presence of demi-facets, not shown but which are understood to be positioned on the sides of the main vertebral body 6 and which are positioned along opposite upper and downward surfaces of the selected vertebral body portion and which are further understood from an anatomical standpoint to progressively relocate from the top and bottom to the sides of the vertebral body, in particular from the $9^{th}$ through the $12^{th}$ thoracic vertebrae.

Figure 1:
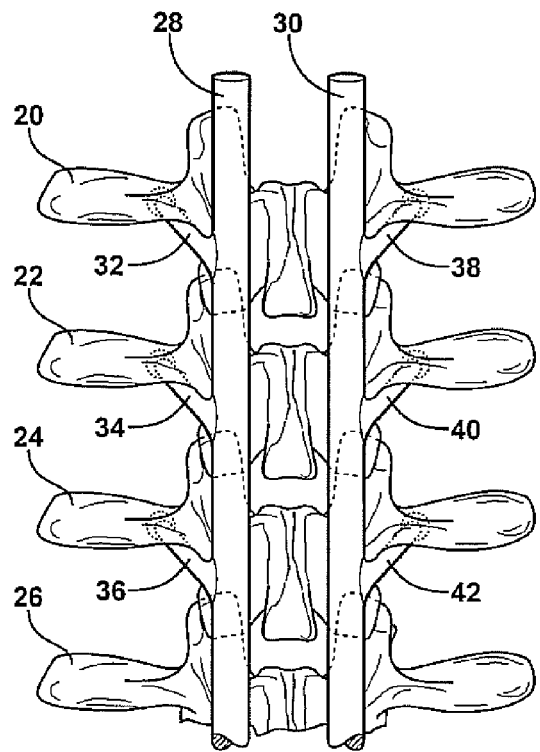
FIG. 1 is a plan view of a plurality of thoracic vertebrae and illustrating a pair of multi-durometer rated and elongated braces secured in lineal extending fashion.
Figure 7A:
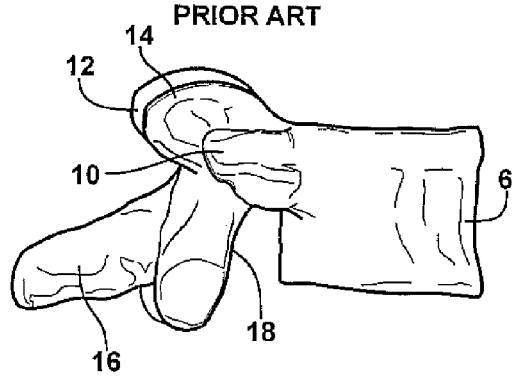
FIG. 7A is a further illustration according to the prior art and which illustrates the various features of a selected thoracic vertebrae.
Figure 8:
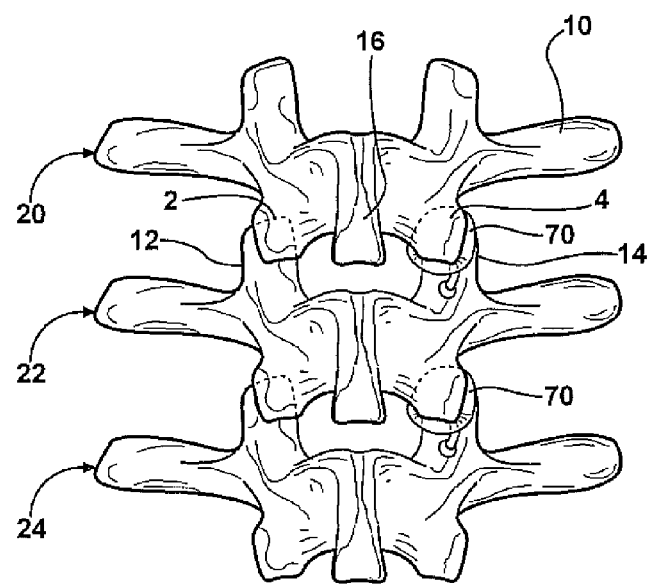
FIG. 8 is an illustration of a subset series of thoracic vertebrae and further showing the provision of a multi-durometer rated plastic inserts for securing at both upper and lower opposing demi-facet locations established between succeeding body portions of each vertebrae.

As will be disclosed in additional detail the recessed configuration of the upper and lower facets (these also being positioned on both of first and second lateral sides as shown in FIGS. 1 and 8) provide for articulation between succeeding vertebrae. Additional features associated with each thoracic vertebrae (and with the exception of the lowermost positioned eleventh and twelfth vertebrae) include transverse processes one of which is evident at 10 in FIG. 7A, upper and associated superior articular processes 12 and 14, a single downwardly and rearwardly extending shin process 16, and a pair of inner and inferior articular processes, see at 18. The inferior articular processes (these best illustrated at 2 and 4 in the cross sectional illustration of FIG. 9B) are fused to a considerable extent with the laminae, and project but slightly beyond their lower borders; their facets are directed forward and a little medialward and downward. The transverse processes arise from the arch behind the superior articular processes and associated pedicles, and are directed obliquely backwards and laterally, with each terminating in a clubbed extremity.

Figure 9:
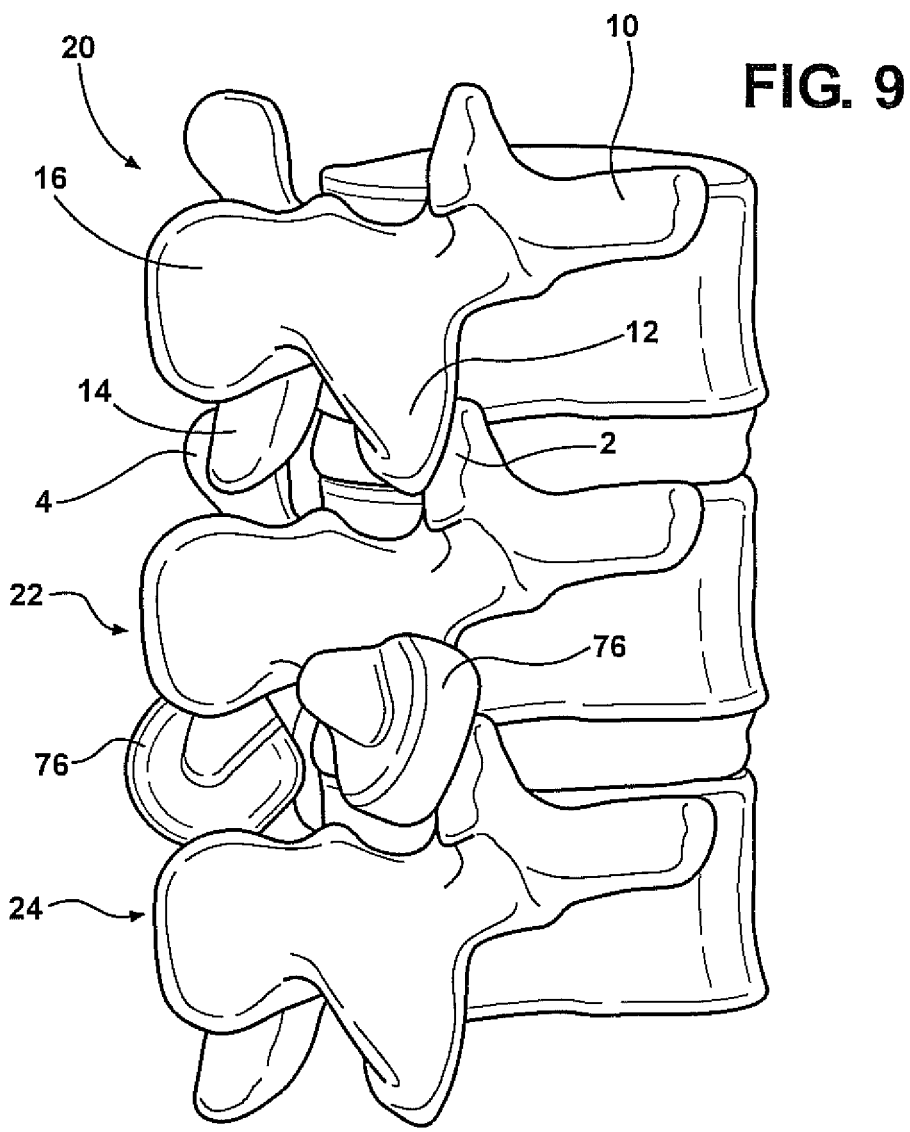
FIG. 9 is a perspective illustration of a plurality of thoracic vertebrae such as also represented in FIG. 8 and illustrating one example of a three dimensional configured insert for assembling over either of a selected inferior or superior articular processes and for providing biasing and cushioning support associated which an opposing process of a succeeding vertebrae.
Figure 9A:
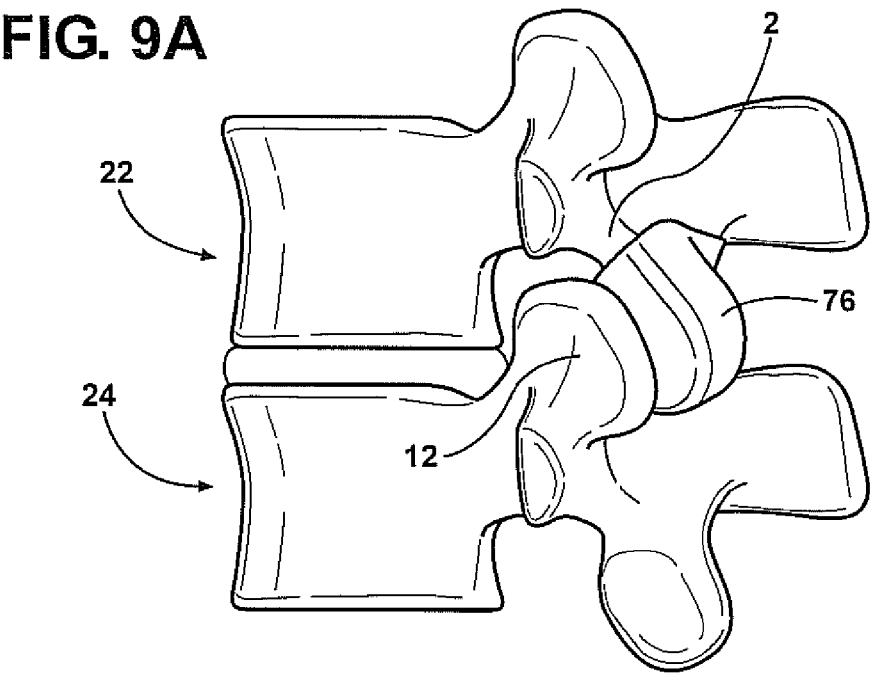
FIG. 9A is a side view of a selected pair of thoracic vertebrae shown in FIG. 9.
Figure 9B:
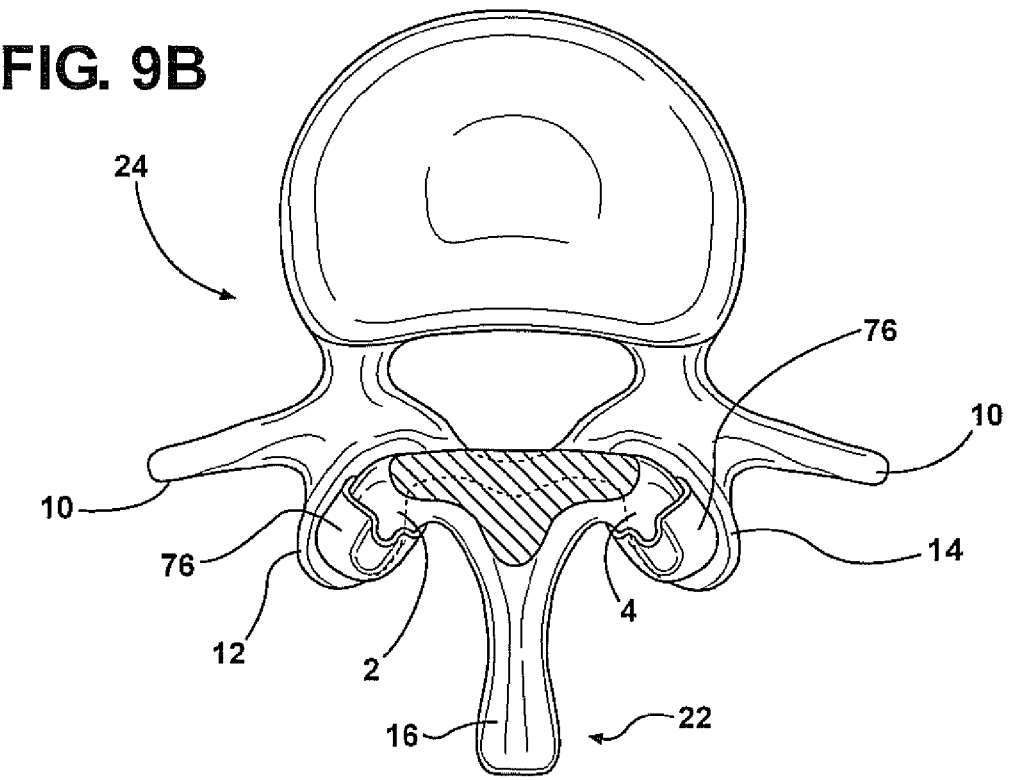
FIG. 9B is a cross sectional cutaway taken from FIG. 9A and illustrating a pair of inserts supported upon opposite inferior articular processes of a selected vertebrae in order to cushion against generally inner configured surfaces associated with the successive vertebrae.

Referring now to FIG. 1 is a plan view is shown of a plurality of thoracic vertebrae, see as further represented at 20, 22, 24, 26, et. seq, and each of which again including the configuration of elements as depicted previously in the prior art illustration of FIG. 7A, as reinforced by the cross sectional view of FIG. 9B. Also illustrated are a pair of multi-durometer rated and elongated braces 28 and 30 secured in lineal extending fashion to each of a selected sub-plurality of the thoracic vertebrae. The braces and insert components according to the several preferred embodiments will be disclosed in use with mounting location particular to the thoracic vertebrae, with the further understanding that these can be redesigned or modified to the extent necessary to permit installation with such as the lumbar or even cervical vertebrae.

Figure 2:
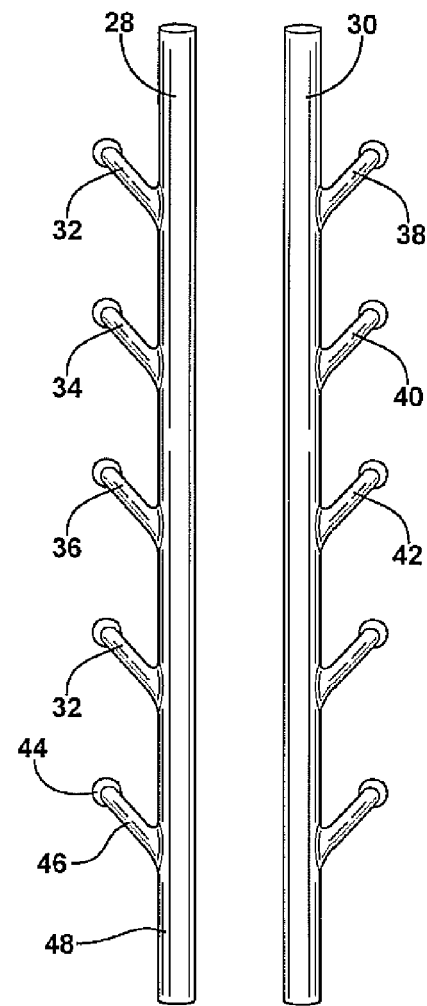
FIG. 2 is an illustration of the pair of vertebral engaging braces in FIG. 1 and showing the configuration of the integrally formed clip portions for mounting the braces to undercut locations defined in each transverse extending process associated with a selected vertebrae.

As also shown in FIG. 2, the pair of vertebral engaging braces 28 and 30 employed in FIG. 1 are constructed of a composite and, typically sanitary and durable plastic material exhibiting any necessary or desired degree of rigidity and flexibility. The braces 28 and 30 each include an elongate stem, from which extend (at any desired angle) integrally formed clip portions (also termed legs) such as which are shown at 32, 34, 36, et. seq. for brace 28 and further at 38, 40, 42, et. seq., for brace 30. Without limitation, the present invention contemplates any plastic or metal material, composite or admixture employed in the creation of the braces or, in further reference to FIG. 8 et seq., the various inserts forming a part of the present invention.

As further shown in FIG. 2, indicated locations 44, 46 and 48 correspond to varied durometer (hardness) rated locations associated with the selected brace 28, with location 44 defining a softest durometer rated portion at an enlarged head or tip location of a selected clip portion (this engaging within a machined undercut location of a selected vertebrae as shown in FIG. 1). An intermediate and connecting location 46 between the enlarged head 44 and the stem corresponds to a likewise intermediate durometer rated portion of the selected vertebral clip. Location 48 further corresponds to a highest durometer rated portion, this corresponding to the stem of the indicated brace 28.

Figure 3:
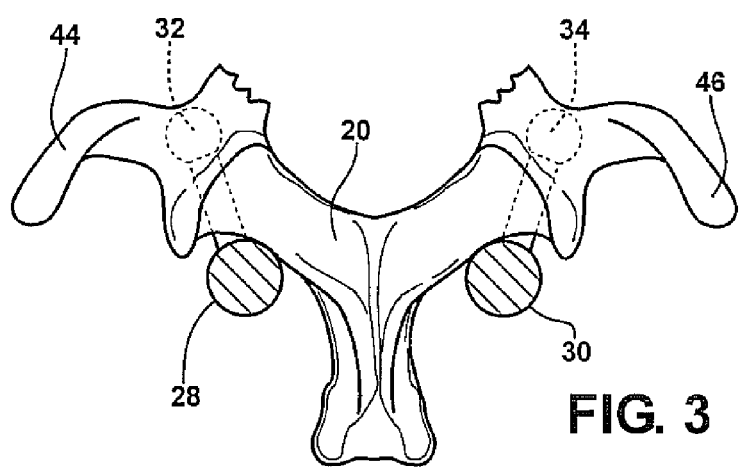
FIG. 3 is a cutaway plan view taken along line 3-3 of FIG. 1 and illustrating the manner in which each of the clip portions associated with the first and second braces secure to their associated transverse process undercut locations.

As again illustrated in FIG. 1, when viewed in combination with the top plan view of FIG. 3, the elongated stems 28 and 30 (following being sectioned to an appropriate length for position-ally interconnecting a selected sub-plurality of thoracic vertebrae) are aligned in generally lengthwise extending fashion with each of the laterally projecting transverse processes associated with the successively positioned vertebrae. It is understood that the elongated braces 28 and 30 can be utilized either singularly or in combination in the manner shown, and so that the braces immobilize the desired number of vertebrae in a similar manner to prior art medical procedures such as fusing, this in order to reduce pain such as resulting from misalignments between the vertebrae and which can further cause pinching of the associated spinal column and branching nerves (not shown).

As further shown in cutaway view of FIG. 3, the elongated braces 28 and 30 are shown with uppermost selected and angularly disposed clip portions 32 and 34, respectively, mounting the braces to undercut locations defined in each transverse extending process (further illustrated in this view at 44 and 46) associated with selected vertebrae 20. As is known, the undercut locations formed in each of the vertebrae can be created by employing a known bone drill with orbital bit, the configuration of the resultant undercut recess firmly engaging the brace upon its selected (and most softest plasticized enlarged clip end) being biasingly inserted within the undercut space. In this fashion, the clip portions associated with each brace are secured within similar undercut locations formed in each of the transverse processes of each of the succeeding vertebrae.

Figure 4:
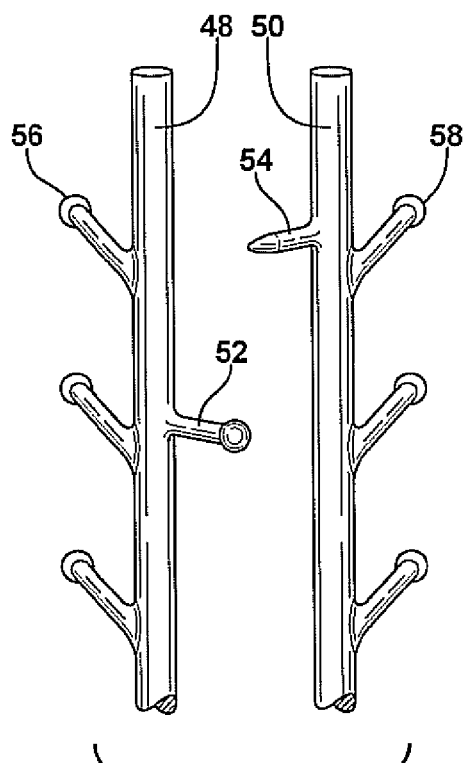
FIG. 4 is an illustration of a pair of modified braces in which additional biasing portions are incorporated into the brace geometry, such as in order to counter a scoliosis condition resulting from misaligned vertebrae.
Figure 5:
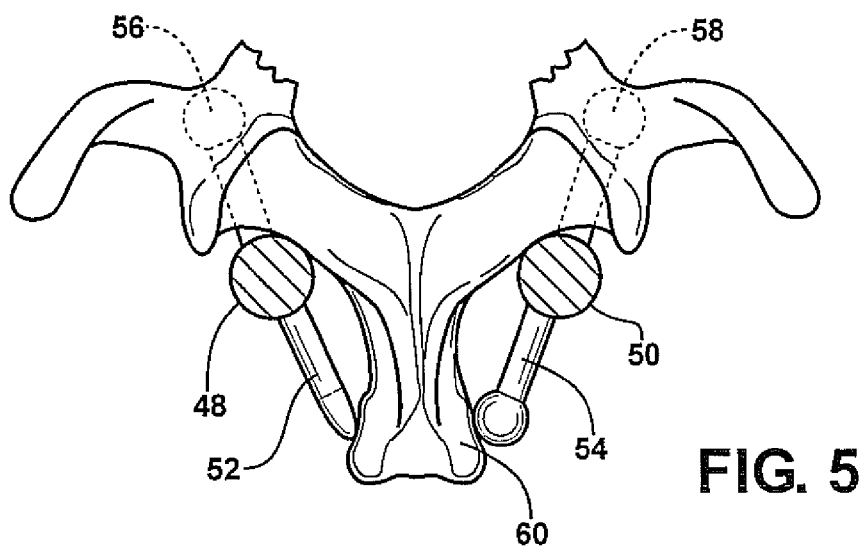
FIG. 5 is a cutaway top plan view illustration, similar to FIG. 3, and illustrating a pair of braces such as shown in FIG. 4 applied in a vertebral environment in which the biasing portions contact the downwardly/rearwardly angled shin process of an associated thoracic vertebrae.

Proceeding to FIG. 4, an illustration is shown at 48 and 50 of a pair of modified composite plastic braces, these being constructed as substantially shown in each of FIGS. 1-3 with plural angular and integral extending engagement clip portions. Each of the redesigned braces 48 and 50 additionally include biasing portions, see selected biasing portions at 52 and 54, which are incorporated into the brace geometry (and as shown extend in another direction in integral fashion from the stem of the associated brace such as at 48), such as in order to counter a scoliosis condition resulting from misaligned vertebrae. This condition is illustrated in the plan cutaway view of FIG. 5 and which illustrates the pair of braces shown in FIG. 4 applied in a vertebral environment (with selected clips 56 and 58 engaging the vertebral transverse processes in likewise undercut machined and resistive fitting manner), and further in which biasing portions 52 and 54 are positioned so that they contact the downwardly/rearwardly angled (and misaligned) shin process 60 of an associated thoracic vertebrae. In this fashion, the modified braces 48 and 50, in addition to stabilizing/immobilizing a selected plurality of vertebrae, provide the additional benefit of addressing (such as by either stabilizing or straightening) a scoliosis condition associated with any sub-plurality of the vertebrae.

Figure 6:
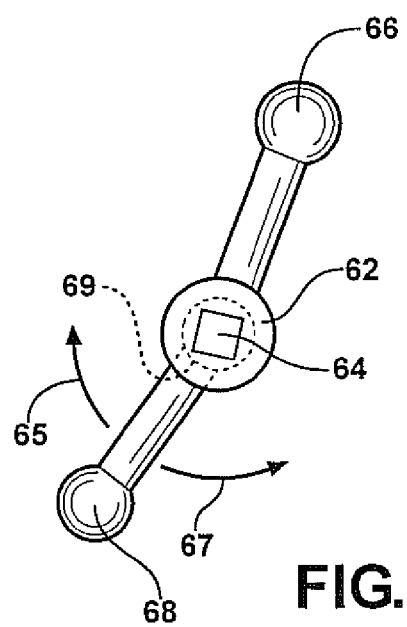
FIG. 6 is a cross sectional illustration of a modified brace and showing the provision of a key access means which allows for the angular repositioning of the extending biasing leg.

Further illustrated in FIG. 6 at 62 is a cross sectional (2D) illustration of a modified brace and showing the provision of a key access means, see key hole 64. A matingly configured bit inserting portion, such associated with such as a screwdriver (not shown), upon being inserted within the key hole 64, allows for the angular repositioning (see directional arrows 65 and 67) of either or both of an integrally formed vertebral engaging clip portion 66 and/or a separately extending biasing leg 68. This is accomplished via any number of rotational adjustable structure incorporated between the stem location (again at 62) of the brace and the respective biasing legs or clips 66 and 68. In on non-limiting possible variant, and although not clearly illustrated, it is envisioned that the inner mounting ends of the legs/clips 66 and 68, as further referenced in phantom at 69 as to clip 68 in FIG. 6, can be mounted within an angular slot or track defined in the stem 62 and such that rotation of the inserting bit results in a limited degree of angular readjustability of the associated clip 68.

Figure 8A:
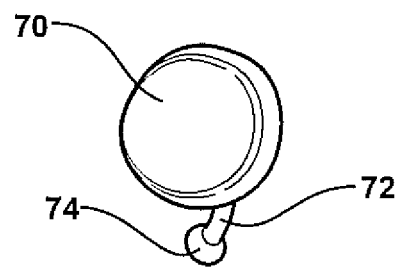
FIG. 8A is a sectional illustration of a selected plastic supporting insert shown in FIG. 8.

Referring now to FIG. 8, an illustration is provided of a subset series of thoracic vertebrae, see again at 20, 22 and 24, and which are supported by the provision of one or more multi-durometer rated plastic inserts 70 (also shown in FIG. 8A) positioned for securing at both upper and lower opposing locations established between succeeding body portions of each vertebrae. As further shown in FIG. 8A, the selected plastic supporting insert 70 exhibits a generally rounded and three dimensional shaped body (such as a generally combination pseudo disk and cushion configuration which can include any of a crescent, arcuate or other 3D profile), and which further includes an integrally formed and extending clip (or angled leg) portion 72 terminating in an enlarged tip portion 74 (the insert 70, clip 72 and enlarged tip 74 again including such as harder to progressively softer durometer rated composite plastics as previously described). The configuration of the supporting insert 70 is such that it can optionally include a biasing (i.e. fluid filled) interior bladder such that, when placed in a generally recessed pocket shaped area identified by opposing superior and inferior articular process locations, provides additional biasing and cushioning support.

FIG. 9 is a perspective illustration of a plurality of thoracic vertebrae such as also represented in FIG. 8 and illustrating one example of a three dimensional configured insert, see pair of inserts shown at 76 for assembling over either of a selected inferior articular process (as shown in particular in FIG. 9B in reference to inferior articular processes 2 and 4). Although not illustrated, it is also understood that the insert 76 can also be reconfigured for mounting over the opposing associated superior articular processes 12 and 14 for providing biasing and cushioning support associated which an opposing process of a succeeding vertebrae.

FIG. 9A is a side view of a selected pair of thoracic vertebrae 22 and 24 shown in FIG. 9. In combination with FIG. 9B again further illustrating a cross sectional cutaway illustrating the pair of inserts 76 supported upon opposite inferior articular processes 2 and 4 of selected vertebrae 22, the inserts 76 are configured so that, upon assembly such as over the inferior articular processes, provide cushioning support at the lateral seating locations established between the inferior and superior articular processes.

Figure 10:
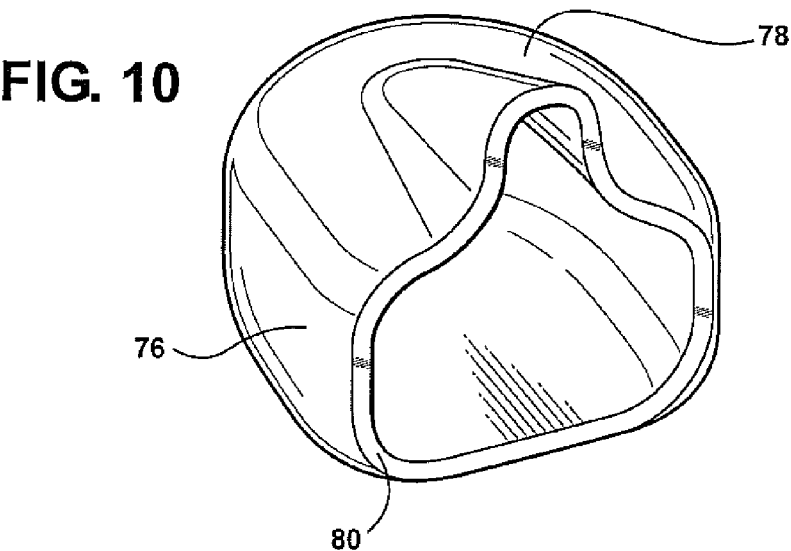
FIG. 10 is a sectional perspective of the three dimensional insert shown in FIG. 9.

Referring now to FIG. 10, a sectional perspective is illustrated in enlarged fashion of the three dimensional shaped insert 76 shown in FIG. 9. Specifically, the insert 76 exhibits a generally arcuate and interiorly hollowed shape and, as previously described, can be constructed of any suitable material (such as a varying durometer plastic but also contemplating a lightweight and ductile metal) exhibiting sufficient flexibility for installation over the extending end portion of the associated spinal process (e.g. inferior articular process as shown).

As further shown in FIG. 10, the pocket defining configuration of the insert 76 includes an edge defined projecting location 78 associated with the overall rim opening 80. In operation, the configuration, including shape and thickness, of the insert 76 can include any of an arcuate, dome, crescent or like shape which facilitates proper fit over the associated spinal process location and in order to establish a cushioning surface at a selected vertebral interface, this further such as to compensate for any misalignment and/or wear associated with the given seating pocket defined between the opposing pair of superior and inferior articular vertebral processes.

Figure 10A:
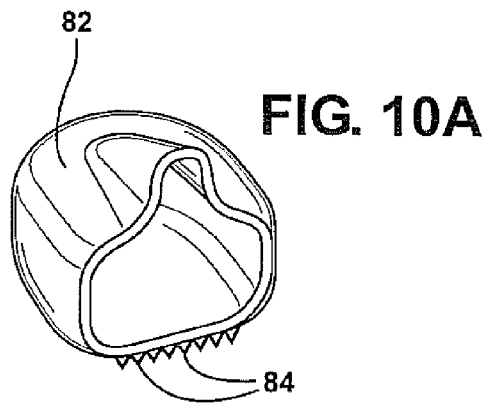
FIG. 10A is a further perspective of a slightly modified insert with a plurality of exteriorly facing teeth.
Figure 10B:
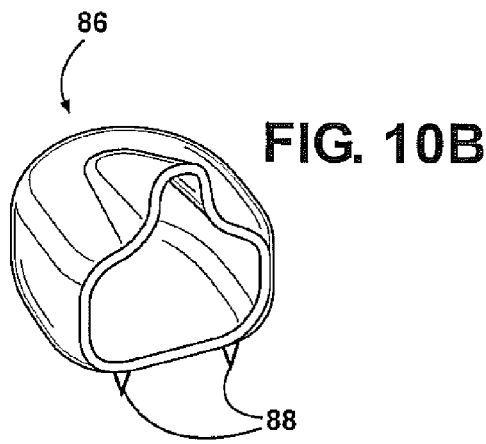
FIG. 10B is a slightly modified perspective compared to that shown in FIG. 10A and by which a pair of spaced teeth are substituted for the plurality of teeth.

FIG. 10A is a further perspective of a slightly modified insert 82 with a plurality of exteriorly facing teeth 84 established along a bottom surface and which facilitates either or both of frictional location as well as bone inducing growth in order to anchor the insert to the associated spinal process. FIG. 10B is a slightly modified perspective illustration 86 of an insert, as compared to that shown in FIG. 10A and by which a pair of spaced teeth 88 are substituted for the plurality of teeth.

Figure 10C:
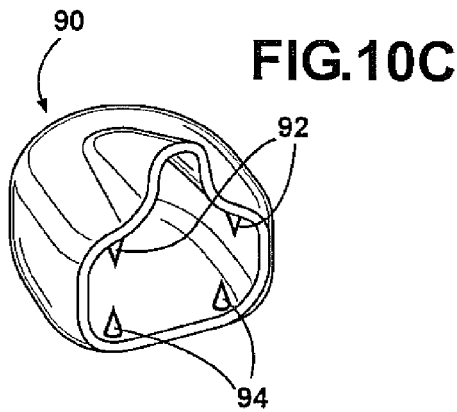
FIG. 10C is a further modified perspective in which pairs of opposing and inward facing teeth are substituted to improve mounting to a selected inferior articular process.
Figure 10D:
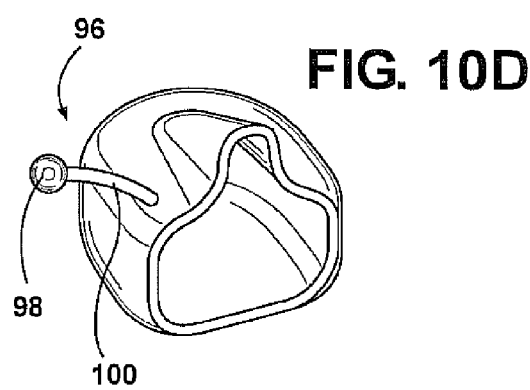
FIG. 10D is an illustration of an undercut mounting clip portion extending from the three dimensional insert of FIG. 10.

FIG. 10C is a further modified perspective view of an insert 90 in which pairs 92 and 94 of opposing and inward facing teeth are substituted to improve mounting to a selected inferior articular process. Finally, FIG. 10D is an illustration of a further example 96 of a three dimensional insert and in which an undercut mounting clip portion including an enlarged head 98 which extends from an interconnecting leg 100 of the insert for undercut mounting to a given vertebral bone location and in a similar fashion as previously described in reference to the clip in FIG. 8A.

Figure 11:
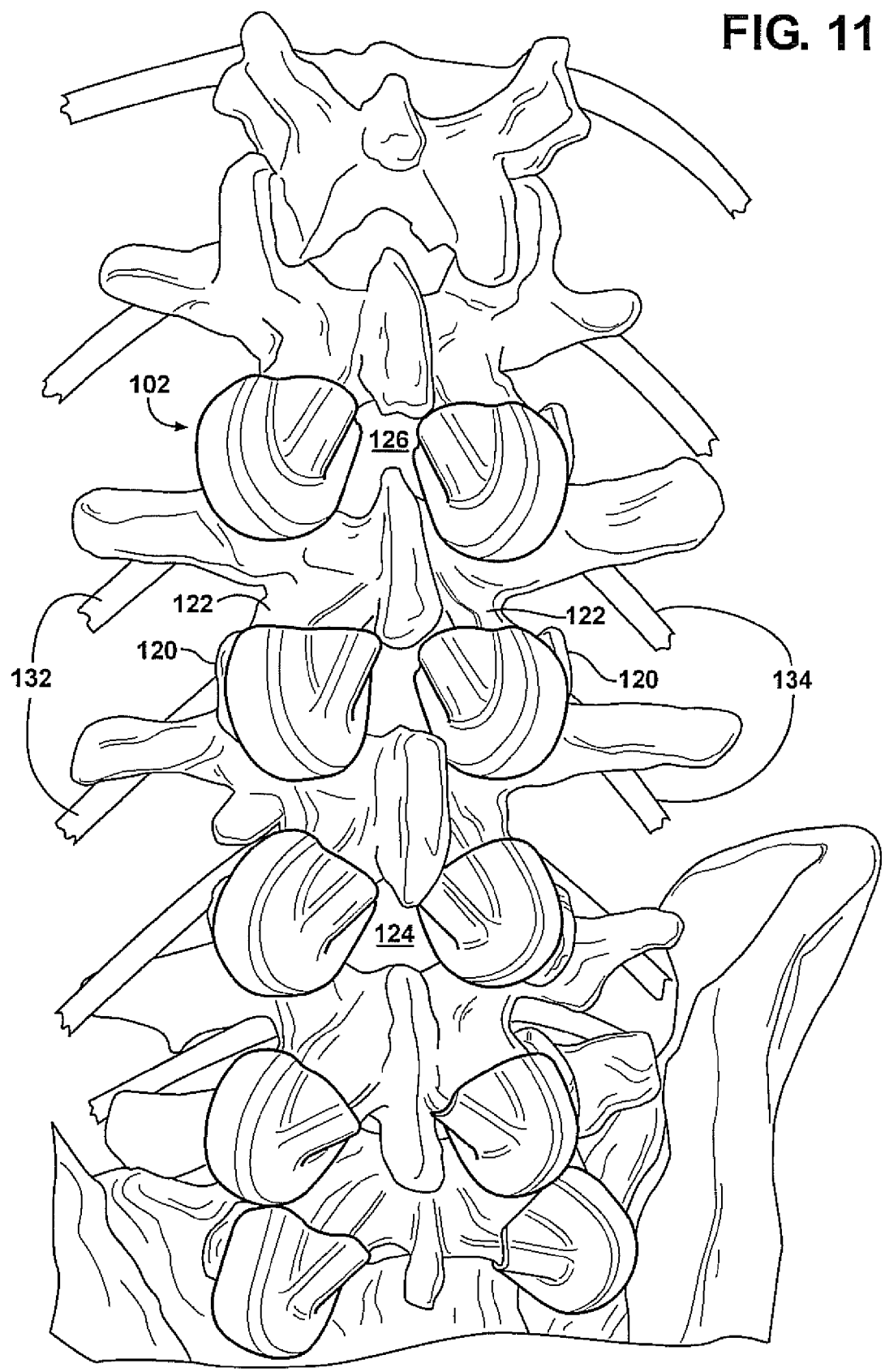
FIG. 11 is an environmental illustration of a lower range of a human vertebral column and which illustrates multiple pairs of pocket defining implants supported upon the downwardly/rearwardly angled inferior articular processes extending from a main body of a first selected vertebra, the implants exhibiting desired wall thicknesses for establishing a desired separation distance between the inferior articular process facets and opposing superior articular process facets in order to prevent pinching of the associated spinal nerve branches.
Figure 12:
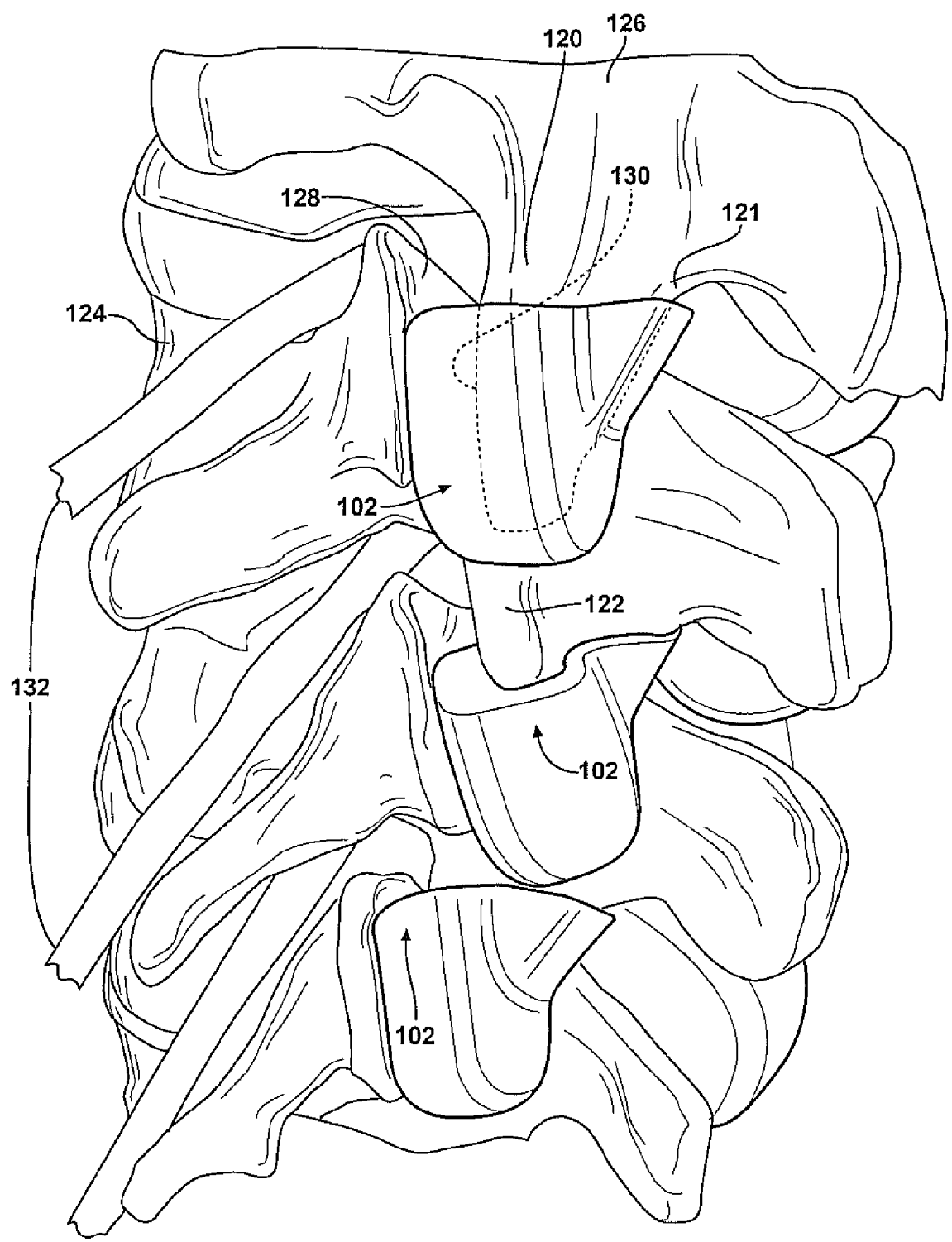
FIG. 12 is a rotated and enlarged view of FIG. 11 and better illustrating the separation dimensions between the overlapping and articulating superior and inferior articular process facets established by the pocket shaped implants of the present invention.

With reference now to FIGS. 11-15, a number of variations of pocket implants are shown, such as generally at 102 in each of FIGS. 11-13, for assisting in providing a correct separation distance between overlapping superior and inferior articular processes. The implant 102 is capable of being utilized with a variety of differently configured vertebrae (both human and other mammalian) however, and as depicted, is particularly associated with succeeding lumbar vertebrae (L1-L5) and upper successive thoracic vertebrae (Th1-Th12).

The implant 102, as best shown individually in FIG. 13, exhibits a three dimensional shaped body having an arcuate or curved exterior profile and which is constructed of a medical grade plastic, composite or other suitable material exhibiting the necessary properties of flexibility and durability. The body as likewise shown in two dimensional end profile exhibits a generally arcuate open rim edge profile including interconnected bottom 104 and sides 106 and 108. A top rim edge portion is further exhibited by reverse arcuate transition surfaces 110 and 112 portions which terminate in a peak edge 114 (see again FIG. 13). As further shown in three dimension, the peak 114 converges along a depth extending protuberance 116 to converge into an upper most surface 118 of the body.

In this fashion, the configuration of the body is such that the rim edge defines an open interior and three dimensional extending pocket, this as best generally referenced in FIG. 13. As also shown in FIG. 12, the implant 102 is capable of being mounted (such as by adhesively gluing or affixing by any other mechanical or chemical structure) over the downwardly/rearwardly angled tip of either or both of the inferior articular processes associated with each concerned vertebra, again as clearly depicted in either of FIG. 11 or 12.

The tip of the inferior articular process, see at 120, covered by the mounted implant 102 is shown in phantom in FIG. 12 and further depicts the manner in which the peak 114 accommodates the edge profile 121 of the process 120. As further shown, the inferior articular processes 120 project downwardly from the main vertebral bodies in paired fashion, with the superior articular processes (at 122) likewise projecting upwardly, both in paired fashion and which is depicted for successive vertebrae 124 and 126 in FIG. 11. In human vertebral physiology, the superior processes 120 and inter-abutting and articulating inferior processes 122 project respectively upward and downward from the junctions of pedicles and laminae of each vertebra (not depicted in perspective for purposes of clarity of illustration).

As further best shown in FIGS. 11-12, the facets on the superior processes (see at 128 in FIG. 12) are concave, and look backward and medialward, with those on the inferior processes (further at 130 in phantom in FIG. 12) being convex and directed forward and lateralward. As is also best depicted in FIG. 11, the superior processes 120 are dimensioned to be wider apart and overlap the inferior processes 122, thereby creating an articulated column in which the inferior articular processes are embraced by the superior processes of the subjacent vertebra.

As further depicted in FIGS. 11-12, each implant 102 teaches a pocket defining insert having a variable wall thickness, and which are employed individually or in paired fashion between each laterally spaced pair of overlapping facet contact locations established between inwardly facing superior articular process facets (such as shown at 128 in FIG. 12) associated with a first (lower) vertebra and opposing outwardly facing inferior articular process facets (such as further shown at 130) associated with a second (upper succeeding) vertebra (best depicted in side perspective in FIG. 12). The implants 102 are capable of being utilized singularly or in paired fashion with respect to the opposing and inter-articulating pairs of superior and inferior articular processes, this in order to customize an implant configuration in order to properly rehabilitate and repair a damaged vertebral column in a manner to provide proper and non-pinching passage of the spinal nerve branches 132 and 134 outwardly from the central spinal cord (not shown) and through the lateral spaces established between the vertebrae.

FIG. 14 is an end view illustration of the pocket implant of FIG. 13 and again illustrating the configuration of the various interconnecting profile edges 104, 106, 108, 110, 112 and 114. One non-limiting aspect of the implant 102 is the ability to vary the thickness dimension of any one or more of the individual interconnecting edges, this in order to re-establish a desired spatial relationship between the opposing articular process facets 128 and 130 depicted in FIG. 12.

In particular, dimension 136 in FIG. 14 represents a thickness of the base or bottom interconnecting rim edge 104, this further shown in FIG. 12 as an equivalent separation distance between the facets 128 and 130 of the superior and inferior articular processes. A range of material thicknesses, not limited to such as 1-5 mm, can be incorporated into the design of the implant 102, this in order to re-establish the desired relationship of the articulating support location as shown. It is further envisaged that the exterior surface of the bottom rim edge 104 can exhibit a convex or protuberant projection (see in phantom at 138 in FIG. 13), this in order to mimic the natural facet surface 130 of the inferior articular process over which the implant 102 is installed and in order to properly seat and inter-articulate with the concave recess profile of the opposing superior articular process facet 128.

FIG. 15 is an end view illustration a variation of implant, generally at 140, exhibiting a different edge extending profile and associated wall thickness, such as for accommodating a different spatial relationship established between articulating superior/inferior processes. In particular, the implant 140 depicts interconnected bottom 142, side, 144/146, upper transitioning 148/150 and top or peak 152 edges. Depending upon the shaping of the articular process 120 over which the implant 140 is to be mounted, the dimensioning of any one or more of the sides can be altered in order to establish a desired support relationship between the vertebrae. As shown, this includes a thickness dimension of the bottom edge 142 being slightly less than that depicted for corresponding edge 104 (dimension 136) in FIG. 14.

Finally, FIG. 16 is a further end view variation of a pocket implant 154 similar to those depicted in FIGS. 14-15 and illustrating different wall thicknesses shown by interconnected bottom 156, side, 158/160, upper transitioning 162/164 and top or peak 166 edges. In comparison to FIGS. 14-15, the bottom edge 156 exhibits an even lesser thickness dimension.

Having described my invention, other and additional preferred embodiments will become apparent to those skilled in the art to which it pertains, and without deviating from the scope of the appended claims. This can include providing the implants in a kit form according to varying dimensions and so that a surgeon can quickly identify a desired separation distance to be established (or re-established) at a typically damaged inter-vertebral location between the seating and articulating process facets.

It is also envisioned that the implant shapes can be produced on-demand using novel three dimensional printing assemblies and techniques, such capable of being quickly accomplished during the course of the associated medical procedure and in order to guarantee the availability and fit of a desired implant configuration tailored to fit the physiology of the patient's vertebra. Finally, and while the shaping of the inferior articular process suggests using this as the basis for mounting the implant in a cap or cover attaching manner, it is also envisioned that the body can be redesigned as necessary and in order to be mounted over the superior articular process and associated facet 128 and to face inwardly in contact with an uncovered inferior articular facet 130.

I claim:

1. An implant for assisting in providing a correct separation distance between overlapping superior and inferior articular processes of succeeding vertebrae, comprising:
    a body exhibiting a generally arcuate shape having an exposed rim edge profile defining an interior extending pocket, said rim edge profile including a bottom, sides, and an upper most surface, a top rim edge portion incorporated into said uppermost surface and exhibiting reverse arcuate transition surfaces which extend from an outwardly arcuate peak edge and converge into said upper most surface such that said rim edge profile establishes a depth extending protuberance upon said body and further such that said body is adapted to being mounted in supported fashion over a tip of an inferior articular process of a first selected vertebrae; and
    an exterior surface of said body establishing an inferior articular facet which contacts an opposing superior articular facet of a succeeding vertebrae to provide correct lateral spacing between the superior and inferior processes for accommodating laterally extending nerve branches of the spinal nerve column between the vertebrae.

2. The implant as described in claim 1, further comprising a pair of said implants being employed in paired fashion between each laterally spaced pair of overlapping facet contact locations established between inwardly facing superior articular process facets associated with a first lower vertebra and opposing outwardly facing inferior articular process facets associated with a second upper succeeding vertebra.

3. The implant as described in claim 1, further comprising said body constructed of a medical grade plastic, composite or other suitable material exhibiting the necessary properties of flexibility and durability.

4. The implant as described in claim 1, further comprising a thickness in a range of 1-5 mm associated with said bottom edge of said rim profile.

5. The implant as described in claim 1, further comprising an exterior surface of said bottom rim edge exhibiting any of a convex or protuberant projection.

* * * * *